United States Patent [19]

Berg et al.

[11] Patent Number: 5,250,157

[45] Date of Patent: Oct. 5, 1993

[54] SEPARATION OF TOLUENE FROM METHYL ISOBUTYL KETONE BY AZEOTROPIC DISTILLATION

[75] Inventors: Lloyd Berg, 1314 S. Third Ave., Bozeman, Mont. 59715; Randi W. Wytcherley, Bozeman, Mont.

[73] Assignee: Lloyd Berg, Bozeman, Mont.

[21] Appl. No.: 20,397

[22] Filed: Feb. 22, 1993

[51] Int. Cl.$^5$ .......................... B01D 3/36; C07C 7/06; C07C 45/84

[52] U.S. Cl. .......................... 203/63; 203/68; 203/70; 568/410; 585/864; 585/866; 585/867

[58] Field of Search .......................... 203/63, 68, 70; 568/410; 585/804, 806, 864, 866, 867

[56] References Cited

U.S. PATENT DOCUMENTS

| | | | |
|---|---|---|---|
| 2,265,220 | 12/1941 | Sullivan | 203/63 |
| 2,544,562 | 3/1951 | Michael | 568/410 |
| 2,871,169 | 1/1959 | Martin | 568/410 |
| 3,265,592 | 8/1966 | Van Der Weel | 568/410 |
| 3,276,973 | 10/1966 | Burmaster | 568/410 |
| 4,163,696 | 8/1979 | Wong | 568/410 |

OTHER PUBLICATIONS

*Azeotropic Data-III*, Horsley, Publ. by American Chemical Society, Washington, D.C., 1973 pp. 202, 246-247, 253.

*Primary Examiner*—Wilbur Bascomb, Jr.

[57] ABSTRACT

Toluene cannot be separated from methyl isobutyl ketone by conventional distillation or rectification because of the minimum boiling azeotrope. Toluene can be readily separated from methyl isobutyl ketone by using azeotropic distillation. Typical examples of effective agents are 1-butanol, 2-methoxyethanol and n-heptane.

2 Claims, No Drawings

1

SEPARATION OF TOLUENE FROM METHYL ISOBUTYL KETONE BY AZEOTROPIC DISTILLATION

FIELD OF THE INVENTION

This invention relates to a method for separating toluene from methyl isobutyl ketone using certain organic compounds as the agent in azeotropic distillation.

DESCRIPTION OF PRIOR ART

Azeotropic distillation is the method of separating close boiling compounds from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

Toluene, B.P. 110.75° C. and methyl isbutyl ketone, B.P. 116° C. form a minimum azeotrope boiling at 110.7° C. and containing 3% methyl isobutyl ketone and therefore are impossible to separate by distillation or rectification. Azeotropic distillation would be an attractive method to break this azeotrope and separate toluene from methyl isobutyl ketone by rectification.

TABLE 1

Theoretical and Actual Plates Required vs. Relative Volatility for Toluene - Methyl Isobutyl Ketone Separation

| Relative Volatility | Theoretical Plates Required At Total Reflux, 95% Purity | Actual Plates Required, 75% Eff. |
|---|---|---|
| 1.12 | 52 | 70 |
| 1.20 | 33 | 44 |
| 1.25 | 27 | 36 |
| 1.30 | 23 | 31 |
| 1.40 | 18 | 24 |
| 1.60 | 13 | 17 |

The advantage of using azeotropic distillation in this separation can be seen from the data shown in Table 1. If an agent can be found that will increase the relative volatility to 1.6, only seventeen actual plates are required for 95% purity.

TABLE 2

Effective Azeotrope Formers to Separate Toluene From Methyl Isobutyl Ketone

| Compounds | Relative Volatility |
|---|---|
| 1-Propanol | 1.27 |
| 1-Butanol | 1.60 |
| Isobutanol | 1.32 |
| 2-Methoxyethanol | 1.7 |
| Methyl cyclohexane* | 1.07 |
| n-Heptane* | 1.18 |

*Brings methyl isobutyl ketone out as overhead

OBJECTIVE OF THE INVENTION

The objects of this invention are to provide a process or method of azeotropic distillation that will enhance the relative volatility of toluene to methyl isobutyl ketone in their separation in a rectification column. It is a further object of this invention to identify certain organic compounds which are effective as azeotropic distillation agents, that are stable and can be readily separated from toluene and can be recycled to the azeotropic distillation column with little decomposition.

SUMMARY OF THE INVENTION

The objects of the invention are provided by a process for the separation of toluene from methyl isobutyl ketone which entails the use of certain organic compounds as the agent in azeotropic distillation.

DETAILED DESCRIPTION OF THE INVENTION

We have discovered that certain organic compounds will effectively increase the relative volatility between toluene and methyl isobutyl ketone by rectification when employed as the agent in azeotropic distillation. Table 2 summarizes the data obtained with these agents in a rectification column. The agents which are effective are 1-propanol, 1-butanol, isobutanol, 2-methoxyethanol, methyl cyclohexane and n-heptane.

THE USEFULNESS OF THE INVENTION

The usefulness or utility of this invention can be demonstrated by referring to the data presented in Tables 1 and 2. All of the successful agents show that toluene can be separated from methyl isobutyl ketone by means of azeotropic distillation in a rectification column and that the ease of separation as measured by relative volatility is considerable.

WORKING EXAMPLES

EXAMPLE 1

One hundred grams of the toluene-methyl isobutyl ketone azeotrope and fifty grams of 1-butanol were charged to a glass perforated plate rectification column containing 7.3 theoretical plates. After five hours at total reflux, overhead and bottoms samples were taken and analysed by gas chroma tography. The overhead was 99.8% toluene, 0.2% methyl isobutyl ketone; the bottoms was 93.9% toluene, 6.1% methyl isobutyl ketone which is a relative volatility of 1.6.

EXAMPLE 2

One hundred grams of the toluene-methyl isobutyl ketone azeotrope and 100 grams of 2-methoxyethanol were charged to the glass perforated plate rectification column containing 7.3 theoretical plates. After six hours at total reflux, the overhead analysis was 99.6% toluene, 0.4% methyl isobutyl ketone; the bottoms analysis was 85.0% toluene, 15.0% methyl isobutyl ketone which is a relative volatility of 1.7.

EXAMPLE 3

One hundred grams of the toluene-methyl isobutyl ketone azeotrope and fifty grams of n-heptane were charged to the glass perforated plate column containing 7.3 theoretical plates. After five hours at total reflux, the overhead analysis was 11% methyl isobutyl ketone, 89% toluene; the bottoms analysis was 3.5% methyl isobutyl ketone, 96.5% toluene which is a relative volatility of 1.18.

We claim:

1. A method for recovering toluene from a mixture of toluene and methyl isobutyl ketone which comprises distilling a mixture of toluene and methyl isobutyl ketone in the presence of an azeotrope forming agent, recovering the toluene and the azeotrope forming agent as overhead product and obtaining the methyl isobutyl ketone from the stillpot, wherein said azeotrope forming agent is 2-methoxyethanol.

2. A method for recovering methyl isobutyl ketone from a mixture of methyl isobutyl ketone and toluene which comprises distilling a mixture of methyl isobutyl ketone and toluene in the presence of an azeotrope forming agent, recovering the methyl isobutyl ketone and the azeotrope forming agent as overhead product and obtaining the toluene from the stillpot, wherein said azeotrope forming agent comprises a material selected from the group consisting of methyl cyclohexane and n-heptane.

* * * * *